United States Patent [19]

Stirling et al.

[11] Patent Number: 5,346,828
[45] Date of Patent: Sep. 13, 1994

[54] STEREOISOMERIC ENRICHMENT OF 2-AMINO-3-HYDROXY-3-PHENYLPROPIONIC ACIDS USING D-THREONINE ALDOLASE

[75] Inventors: David I. Stirling, Fanwood; Muppala S. Raju, Bridgewater; Andrew L. Zeitlin, Somerville, all of N.J.

[73] Assignee: Celgene Corporation, Warren, N.J.

[21] Appl. No.: 844,724

[22] Filed: Mar. 2, 1992

Related U.S. Application Data

[63] Continuation-in-part of Ser. No. 689,300, Apr. 22, 1991, abandoned, and Ser. No. 676,102, Mar. 27, 1991, abandoned.

[51] Int. Cl.$^5$ .............................. C12P 41/00
[52] U.S. Cl. ................... 435/280; 435/829
[58] Field of Search ................ 435/280, 829

[56] References Cited

U.S. PATENT DOCUMENTS

| | | | |
|---|---|---|---|
| 3,871,958 | 3/1975 | Nakazawa et al. | 195/29 |
| 4,235,892 | 11/1980 | Nagabhushan | 424/226 |
| 4,492,757 | 1/1985 | Kato et al. | 435/280 |
| 4,582,918 | 4/1986 | Nagabhushan et al. | 549/525 |
| 4,677,214 | 6/1987 | Nagabhushan et al. | 549/551 |
| 4,945,181 | 7/1990 | Dick et al. | 564/212 |

OTHER PUBLICATIONS

Cambou B. et al, Biotechnol and Bioengineering XXVI:1449–1454 (1984).
Jones J., Tetrahedron 42:3351–3403 (1986).
Cutler et al., JACS, 74, 5475–5481, 1952.
Suter et al., JACS, 75, 4330–4333, 1953.
Kleeman et al., Pharmazeutische Wirkstoffe, 874–875, 1987.
Drugs of the Future, VII, No. 3, 172–174, 1982.

Primary Examiner—Douglas W. Robinson
Assistant Examiner—S. Saucier
Attorney, Agent, or Firm—Mathews, Woodbridge & Collins

[57] ABSTRACT

Mixtures of enantiomeric D,L-threo 2-amino-3-hydroxy-3-phenylpropionic acids can be stereoisomerically enriched by contacting the mixture with a D-threonine aldolase. In a typical embodiment, D- and L-threo 2-amino-3-hydroxy-3-(4-methylsulfonylphenyl)propionic acid is treated with D-threonine aldolase to produce L-threo 2-amino-3-hydroxy-3-(4-methylsulfonylphenyl)propionic acid with a high ee. The benzaldehyde and amino acid formed from the D-threo isomer can be recycled.

17 Claims, No Drawings

STEREOISOMERIC ENRICHMENT OF 2-AMINO-3-HYDROXY-3-PHENYLPROPIONIC ACIDS USING D-THREONINE ALDOLASE

CROSS-REFERENCE TO RELATED APPLICATIONS

This is a continuation-in-part of Ser. No. 07/689,300 filed Apr. 22, 1991 and of Ser. No. 07/676,102 filed Mar. 27, 1991, both now abandoned.

DETAILED DESCRIPTION

The present invention relates to the stereoisomeric enrichment of 2-amino-3-hydroxy-3-phenylpropionic acids.

The biological activity of many chemical compounds such as pharmaceutical and agricultural products which possess a center of chirality often is found to reside principally in one of the chiral forms. Since most chemical syntheses inherently are not stereoselective, this poses a serious chemical processing problem. Enrichment in favor of one chiral form thus will be required at some stage, either the final chiral compounds or the chemical precursors which possess the same center of chirality. Whatever stage is selected for the enrichment, and in the absence of a method of recycling of the unwanted stereoisomer(s), the process inherently is limited to a maximum yield of $1/(2^n) \times 100\%$ for the desired stereoisomer, where n is the total number of chiral centers in the molecule.

2-Amino-3-hydroxy-3-phenylpropionic acids and derivatives thereof are used as intermediates in the synthesis of a number of biologically useful chemical compounds. L-threo 2-amino-3-hydroxy-3-(4-methylsulfonylphenyl)propionic acid thus is an intermediate in the synthesis of the antibiotics D-threo 1-fluoro-2-(dichloroacetamido)-3-(4-methylsulfonylphenyl)propan-1-ol (also known as florfenicol) and D-threo 2-(dichloroacetamido)-3-(4-methylsulfonylphenyl)propane-1,3-diol (also known as thiamphenicol). In addition, L-threo 2-amino-3-(4-methylthiophenyl)-3-hydroxypropionic acid is an intermediate in the synthesis of antibiotics. Similarly, L-threo 2-amino-2-methyl-3-hydroxy-3-phenylpropionic acid is an intermediate in the production of L-2-amino-2-methyl-3-(3,4-dihydroxyphenyl)-propionic acid (also known as L-methyldopa).

Because 2-amino-3-hydroxy-3-phenylpropionic acid and its derivatives possess two chiral centers, there exists four stereoisomers. These include two pair of enantiomers, the D,L-erythro and the D,L-threo enantiomers. Where the final product retains two chiral centers, generally only one stereoisomer, typically the L-threo stereoisomer, is useful for the production of biologically active compounds. (In the production of L-methyldopa, the "erythro" and "threo" distinction is not important since hydrogenation eliminates the chiral center associated with the 3-hydroxy group of 2-amino-2-methyl-3-hydroxy-3-phenylpropionic acid, i.e., the final product has only one chiral center. Again, however, only one enantiomer, the L-form, is useful.) When two chiral centers are present, the desired stereoisomer must be separated or enriched from mixtures of the D,L-erythro and D,L-threo stereoisomers in order to more efficiently produce the final compound in high optical purity.

British Patent No. 1,268,867, to Akiyama et al., which is incorporated herein by reference, describes a procedure for preparing thiamphenicol in which an alcoholic solution of an alkalai metal salt of glycine is contacted with two moles of p-methylsulfonylbenzaldehyde per mole of glycine in the presence of an alkali metal carbonate to produce mixtures rich in the D,L-threo enantiomeric forms of β-(4-methylsulfonylphenyl)serine (rather than the D,L-erythro forms). Separation of the L-threo enantiomer from the D-threo enantiomer then is performed using conventional chemical resolution. Yields, however, are inherently low, being limited to no more than 50% of the threo mixture.

The present invention represents a significant improvement in the preparation of L-threo 2-amino-3-hydroxy-3-phenylpropionic acids, 2-amino-2-methyl-3-hydroxy-3-phenylpropionic acids, and derivatives thereof which are unsubstituted or substituted in the phenyl ring. By subjecting a mixture of the D-threo and L-threo forms of a 2-amino-3-hydroxy-3-phenylpropionic acid, generally but not necessarily racemic, to the action of D-threonine aldolase, selective cleavage of the D-threo 2-amino-3-hydroxy-3-phenylpropionic acid to glycine and the corresponding benzaldehyde occurs without substantial cleavage of L-threo 2-amino-3-hydroxy-3-phenylpropionic acid. Likewise, by subjecting the D,L-threo 2-amino-2-methyl-3-hydroxy-3-phenylpropionic acid enantiomeric mixture to the action of D-threonine aldolase according to the present invention, selective cleavage of the D-threo 2-amino-2-methyl-3-hydroxy-3-phenylpropionic acid to alanine and the corresponding benzaldehyde occurs without substantial cleavage of L-threo 2-amino-2-methyl-3-hydroxy-3-phenylpropionic acid. In each case, the corresponding benzaldehyde and the amino acid can be recovered readily from the reaction mixture for recycling.

The present invention is based on the discovery that the action of D-threonine aldolase selectively cleaves the bond between the carbon atom in the 2-position (the carbon atom carrying the amino group) and that in the 3-position (the carbon atom carrying the hydroxy group) in a D-threo 2-amino-3-hydroxy-3-phenylpropionic acid or D-threo 2-amino-2-methyl-3-hydroxy-3-phenylpropionic acid while leaving the corresponding L-threo isomer substantially intact. Thus the present invention is especially suitable for use in the preparation of the biological compounds described above, e.g., florfenicol, thiamphenicol, and L-methyldopa.

In the broadest sense, the present invention involves enantiomerically enriching a mixture of D,L-threo 2-amino-3-hydroxy-3-phenylpropionic acids or D,L-threo 2-amino-2-methyl-3-hydroxy-3-phenylpropionic acids of the formula:

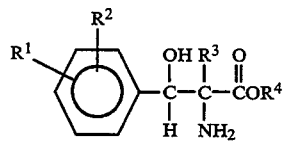

in which each of $R^1$ and $R^2$, independently of the other, is hydrogen, hydroxy, halo, nitro, trifluoromethyl, lower alkyl, lower alkoxy, lower alkylsulfonyl, lower alkylsulfinyl, or lower alkylthio;

$R^3$ is hydrogen or methyl; and $R^4$ is hydrogen or a carboxylic acid protecting group.

Also included are conventional salts of the foregoing 2-amino-2-methyl-3-hydroxy-3-phenylpropionic acids.

The term lower alkyl denotes a univalent saturated branched or straight hydrocarbon chain containing from 1 to 6 carbon atoms. Representative of such alkyl groups are methyl, ethyl, propyl, isopropyl, butyl, isobutyl, sec-butyl, tert-butyl, pentyl, isopentyl, neopentyl, tert-pentyl, hexyl, isohexyl, and the like.

The term lower alkoxy refers to a lower alkyl joined to the remainder of the molecule through an ethereal oxygen bond, as for example methoxy, ethoxy, propoxy, isopropoxy, butoxy, pentoxy, hexoxy, and the like.

Halo refers to chloro, bromo, fluoro, and iodo.

A carboxy group can be protected by $R^4$ as an ester group which is selectively removable under sufficiently mild conditions not to disrupt the desired structure of the molecule, especially an alkyl ester of 1 to 12 carbon atoms such as methyl or ethyl and particularly one which is branched at the 1-position such as tert-butyl; and such lower alkyl ester substituted in the 1- or 2-position with (i) lower alkoxy, such as for example, methoxymethyl, 1-methoxyethyl, and ethoxymethyl, (ii) lower alkylthio, such as for example methylthiomethyl and 1-ethylthioethyl; (iii) halogen, such as 2,2,2-trichloroethyl, 2-bromoethyl, and 2-iodoethoxycarbonyl; (iv) one or two phenyl groups each of which can be unsubstituted or mono-, di- or tri-substituted with, for example lower alkyl such as tert.-butyl, lower alkoxy such as methoxy, hydroxy, halo such as chloro, and nitro, such as for example, benzyl, 4-nitrobenzyl, diphenylmethyl, di-(4-methoxyphenyl)methyl; or (v) aroyl, such as phenacyl. A carboxy group also can be protected in the form of an organic silyl group such as tri-lower alkylsilyl, as for example tri-methylsilyloxycarbonyl.

As indicated, the present invention also pertains to the salts of the foregoing compounds with, for example, alkali metals, alkaline earth metals, ammonia and organic amines as, for example, salts in which the cations are sodium, potassium, magnesium, calcium, or the protonated amines such as those derived from ethylamine, triethylamine, ethanolamine, diethylamino-ethanol, ethylenediamine, piperidine, morpholine, 2-piperidinoethanol, benzylamine, procaine and the like. Since the salts are utilized as chemical intermediates, they need not be, but generally are, physiologically acceptable.

The process is particularly well suited for preparing compounds of the formula:

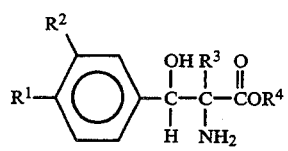

II in which each of $R^1$ and $R^2$, independently of the other, is hydrogen, hydroxy, methoxy, methylsulfonyl, or methylthio;

$R^3$ is hydrogen or methyl; and $R^4$ is hydrogen, $C_1$–$C_3$ alkyl, or a cation (i.e., the salts thereof).

The term "enantiomeric enrichment" as used herein refers to an increase in the amount of one enantiomer as compared to the other. A convenient method of expressing the enantiomeric enrichment achieved is the concept of enantiomeric excess, or "ee", expressed by the expression:

$$ee = \frac{E^1 - E^2}{E^1 + E^2} \times 100$$

in which $E^1$ is the amount of one chiral form (such as the L-threo form) and $E^2$ is the amount of the other chiral form (such as D-threo form). Thus if the initial ratio of the two chiral forms is 50:50 (1:1) and an enantiomeric enrichment sufficient to produce a final ratio of L-threo form to D-threo form of 50:30 (5:3) is achieved, the ee with respect to the L-threo form is 25%. If the final ratio of L-threo form to D-threo form is 70:30 (7:3), the ee with respect to the L-threo form is 40%. Typically, with the process of the present invention, ee's of 85% or greater can be achieved.

Mixtures of the stereoisomeric forms of 2-amino-3-hydroxy-3-phenylpropionic acids or 2-amino-2-methyl-3-hydroxy-3-phenylpropionic acids can be prepared generally by simple condensation of glycine, or alanine, respectively, with an appropriate benzaldehyde using well known procedures. Since this synthesis is not stereoselective, racemic mixtures of the D-threo and L-threo isomers of the corresponding 2-amino-3-hydroxy-3-phenylpropionic acids or 2-amino-2-methyl-3-hydroxy-3-phenylpropionic acids will result.

In the present process, a mixture of D,L-threo 2-amino-3-hydroxy-3-phenylpropionic acid or D,L-threo 2-amino-2-methyl-3-hydroxy-3-phenylpropionic acid is subjected to the action of a D-threonine aldolase. The enzymatic process operates on only one chiral form (or operates on one chiral form to a substantially greater extent than the other). D-threonine aldolase thus not only cleaves the undesired L-isomer, thereby facilitating enrichment of the desired enantiomer, but does so at the bond between the 2-carbon atom and 3-carbon atom of the propionic acid, thereby producing the corresponding benzaldehyde and an amino acid, glycine or alanine. The benzaldehyde and amino acid enzymatic reaction products, however, also are the starting materials used to synthesize the D,L-threo forms of 2-amino-3-hydroxy-3-phenylpropionic acid and 2-amino-2-methyl-3-hydroxy-3-phenylpropionic acid. As such, the reaction products can be recovered and recycled back into the condensation step for further synthesis into 2-amino-3-hydroxy-3-phenylpropionic acid or 2-amino-2-methyl-3-hydroxy-3-phenylpropionic acid, respectively.

For example, a D,L-threo-2-amino-3-hydroxy-3-phenylpropionic acid of Formula I is subjected to the action of D-threonine aldolase:

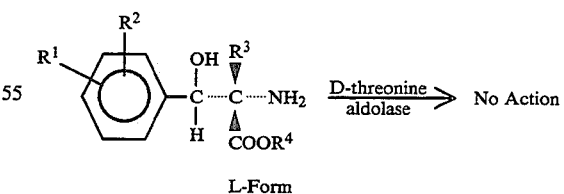

L-Form

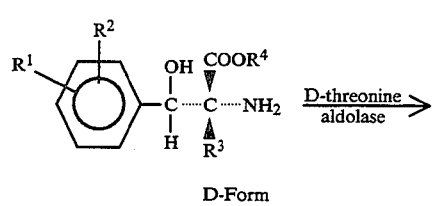

D-Form

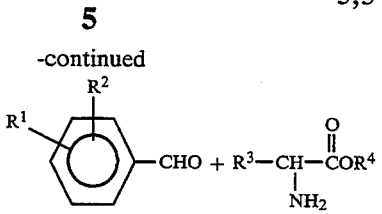

in which each of $R^1$, $R^2$, $R^3$ and $R^4$ are as herein defined.

The D-threonine aldolase enzyme are known and can be prepared for example according to the procedures described by Kato et al., and Yamada et al., infra. The enzyme also can be produced from ubiquitous microorganisms found in soil having no particular history of exposure to threonine. In this latter technique, the microorganisms are cultured and incubated in a suitable growth media and D-threonine, and then subcultured and incubated in a chemostat of growth media and D-threonine. After further incubation, a single colony producing the D-threonine aldolase enzyme can be isolated.

The enzyme can be extracted from the cells using procedures known per se, as for example, by rupturing the cells and recovering the enzyme-containing supernatant. The final enzyme can be used in free, unbound form, either as a cell-free extract or a whole cell preparation, or can be immobilized on a suitable support or matrix such as cross-linked dextran, agarose, silica, polyamide, or cellulose. The enzyme also can be encapsulated in polyacrylamide, alginates, fibers, or the like. Methods for such immobilization are described in the literature (see, for example, *Methods of Enzymology*, 44, 1976).

In the practice of the process, the enzyme is added to mixture of the D- and L-threo-2-amino-3-hydroxy-3-phenylpropionic acids or the D- and L-threo-2-amino-2-methyl-3-hydroxy-3-phenylpropionic acids and the reaction mixture then maintained at enzymatically-active temperatures (approximately 40° C.) until the desired enantiomeric excess of the L-enantiomer is achieved. This point can be readily determined, for example, by chiral HPLC.

It often is advantageous to remove one reactant from the reaction mixture in order to obtain higher ee's through mass action. The reactant need not be physically removed but simply isolated from the enzymatic reaction environment. For example, utilization of a co-solvent in which one of the reaction products is preferentially soluble, will increase the ee. Benzaldehydes are highly soluble in halogenated alkanes such as methylene chloride and chloroform, in lower alkanones (that is, containing from 3 to 10 carbon atoms) such as pentan-2-one or methylisobutyl ketone, and aromatic hydrocarbons such as benzene. Incorporation of such solvents in the reaction mixture will have an advantageous effect. Alternatively, the addition of a nonionic absorbent-type resin such as an Amberlite or Dowex on which the aldehyde adsorbs also will improve the ee through the same principle.

Following or during the enzymatic reaction, the benzaldehyde and amino acid produced can be recycled as previously discussed. The uncleaved L-threo-2-amino-3-hydroxy-3-phenylpropionic acid itself is isolated and processed according to known techniques. For example it can be esterified and then reduced according to previously described techniques to yield the corresponding 2-amino-3-phenylpropane-1,3-diol. If the phenyl group carries a methylsulfonyl group in the 4-position, this diol need merely be dichloroacetylated to yield thiamphenicol. If the phenyl group carries a methylthio group in the 4-position, the diol can be dichloroacetylated and then oxidized as with peracetic acid, again to yield thiamphenicol.

In the preparation of florfenicol, thiamphenicol can be directly fluorinated again using conventional conditions to yield D-threo 2-(dichloroacetamido)-3-(3-methylsulfonylphenyl)-3-fluoropropan-1-ol. Alternatively, L-threo-2-amino-3-hydroxy-3-phenylpropionic acid is esterified and reduced as described above, the amino group is then protected as for example through formation of the phthalimido derivative, this if fluorinated, and, after removal of the amino protecting group the D-threo 2-amino-3-(3-methylsulfonylphenyl)-3-fluoropropan-1-ol is dichloroacetylated as described above.

The following examples will serve to further typify the present invention but should not be construed as a limitation on the scope thereof, which scope is defined solely by the appended claims.

EXAMPLE 1

Racemic D,L-threo 2-amino-3-hydroxy-3-(4-methylthiophenyl)propionic acid (0.7 g) is added to a mixture of 20 mL of 50 mM sodium borate (pH 8.4), 1 mL of 8 mM pyridoxal-5-phosphate, and 4 mL of an extract of D-threonine aldolase. The reaction is maintained at 40° C. until the enantiomeric excess (as determined by chiral HPLC) is no less than 98% of L-threo 2-amino-3-hydroxy-3-(4-methylthiophenyl)propionic acid is obtained, generally about 60–70 minutes under these conditions.

EXAMPLE 2

A mixture of 2.5 g of D-threo 2-amino-3-(4-methylthiophenyl)propane-1,3-diol (obtained by the procedure of Example 1) and 3.6 ml of ethyl dichloroacetate is heated at about 100° C. for approximately three hours. The reaction product is dissolved in ethylene chloride and filtered through activated charcoal. The filtrate is cooled and the filtrate recrystalized from nitroethane to yield D-threo 2-dichloroacetamido-3-(4-methylthiophenyl)-propane-1,3-diol, m.p. 111.6°–112.6° C., $[\alpha]_D^{25} + 12°$ (1% in ethanol).

EXAMPLE 3

L-Threo 2-amino-3-hydroxy-3-(4-methylsulfonylphenyl)propionic acid is obtained from D,L-threo 2-amino-3-hydroxy-3-(4-methylsulfonylphenyl)propionic acid by following the procedure of Example 1. L-Threo 2-amino-3-hydroxy-3-(4-methylsulfonylphenyl)propionic acid then is esterified and reduced as therein described to yield D-threo 2-amino-3-(4-methylsulphonylphenyl)propane-1,3-diol, m.p. 201°–202° C., $[\alpha]_D^{20} - 25.5°$.

D-Threo 2-amino-3-(4-methylsulphonylphenyl)propane-1,3-diol is subjected to dichloroacetylation in a similar fashion to the procedure of Example 2 to yield thiamphenicol, m.p. 164.3°–166.3° C., $[\alpha]_D^{25} + 12.9°$ (1% in ethanol).

Alternatively, thiamphenicol can be obtained from D-threo 2-dicloroacetamido-3-(4-methylthiophenyl)-propane-1,3-diol of Example 2 through oxidation with peracetic acid under conventional conditions.

EXAMPLE 4

Sodium hydroxide (6 g, 150 mmoles) and 8.9 g (100 mmoles) of D,L-alanine are dissolved in 25 mL of water and the solution cooled to around 5° C. while stirring under a nitrogen atmosphere. To the solution is added 21.2 g (200 mmoles) benzaldehyde and the mixture stirred at 5° C. for approximately one hour. The mixture is then warmed to room temperature and maintained for approximately 20 hours. Concentrated hydrochloric acid then is added to bring the reaction mixture to pH 2.0. After stirring the acidic solution for two hours, the aqueous phase is separated, extracted with ethyl acetate and evaporated under vacuum. The resulting material is twice extracted with 80 mL hot absolute ethanol, followed by evaporation of the ethanol. The resulting material is again extracted with 40 mL of absolute ethanol, followed by removal of the ethanol. The extract then is dissolved in at least a 1:1 methanol water solution and absorbed on polymethacrylate column. The column then is eluted with the same 1:1 methanol water solution and the 30 mL fractions are combined and evaporated. Purification on the polymethacrylate column then is repeated using 95% ethanol to yield racemic 2-amino-2-methyl-3-hydroxy-3-phenylpropionic acid.

EXAMPLE 5

The following procedure exemplifies the use of D-threonine aldolase to effect the resolution of racemic mixtures of D,L-threo 2-amino-2-methyl-3-hydroxy-3-phenylpropionic acid to the L-isomer.

D,L-Threo 2-amino-2-methyl-3-hydroxy-3-phenylpropionic acid (14.1 mM) is incubated at pH 8.75 in 50 mM borate buffer and 0.8 mM pyridoxal phosphate with ruptured cells containing approximately 300 μL of enzyme.

At time intervals of approximately 30, 120 and 210 minutes, 200 μL of the incubation mixture are removed and diluted with 800 μL of 1% perchloric acid. After centrifugation of this mixture, the supernatant is analyzed on HPLC. The following illustrates the effectiveness of the enzyme on resolving the racemic mixtures.

|  |  | 30 min. |  | 120 min. |  | 210 min. |  |
| --- | --- | --- | --- | --- | --- | --- | --- |
| Substrate | Enzyme | Total Area[1] | %[2] | Total Area | % | Total Area | % |
| αMφS[3] | 0 | 223 | 0 | 227 | 3.1 | 229 | 3.5 |
| αMφS | 300 μL | 221 | 0 | 237 | 4.6 | 252 | 10.7 |
| αMφS + TφS[4] | 300 μL | 528 | 18.6 | 535 | 21.1 | 540 | 22.4 |
| tφS | 150 μL | 300 | 27.3 | 302 | 32.1 | 301 | 34.6 |
| tφS | 0 | 400 | 0 | 400 | 2.2 | 382 | 3.7 |

[1]Total integration area of the substrate, corresponding benzaldehyde and benzoic acid.
[2]Percentage of total area attributable to benzaldehyde and benzoic acid.
[3]αMφS = α-methylphenylserine {2-amino-2-methyl-3-hydroxy-3-phenylpropionic acid}; 14.1 mM.
[4]TφS = threo phenylserine {2-amino-3-hydroxy-3-phenylpropionic acid}; 13.9 mM.

The L-threo 2-amino-3-hydroxy-3- (4-methylthiophenyl)propionic acid thus obtained then can be esterified and reduced with sodium borohydrate according to known methods to produce D-threo 2-amino-3-(4-methylthiophenyl)propane-1,3-diol, m.p. 151.9°–152.9° C., $[\alpha]_D^{25} -21°$ (1% in ethanol).

EXAMPLE 6

D-threonine aldolase is produced by various microorganisms such as *Alcaligenes faecalis* (deposited in Institute for Fermentation Osaka, Japan under a deposit number IFO-12,669), Pseudomonas DK-2 (deposited in Fermentation Research Institute, Agency of Industrial Science and Technology, Ministry of International Trade and Industry, Japan under deposit number FERM-P No. 6200), and Arthrobacter DK-19, FERM-P No. 6201. See e.g., U.S. Pat. No. 4,492,757 to Kato et al. and Japanese 56-209983 to Yamada et al.

In addition D-threonine aldolase producing microorganisms from soil samples can be isolated as follows.

A soil sample having no particular history of exposure to threonines is inoculated in a shake flask with 50 mL of aqueous media (hereinafter referred to as "media A") which typically contains the following composition concentration:

| | |
| --- | --- |
| $NH_4Cl$ | 1 g/L |
| $MgCl$ | 1 g/L |
| $CaCl_2$ | 0.015 g/L |
| $KH_2PO_4$ | 2.7 g/L |
| NaOH | 0.5 g/L |
| and standard trace element solution | 1 mL/L: |
| $MgSO_4$ | 1 g/L |
| $CaCl_2$ | 0.21 g/L |
| $ZnSO_4.7H_2O$ | 0.2 mg/L |
| $MnSO_4.4H_2O$ | 0.1 mg/L |
| $H_3BO_3$ | 0.02 mg/L |
| $CuSO_4.5H_2O$ | 0.10 mg/L |
| $CuCl_2.6H_2O$ | 0.05 mg/L |
| $NiCl_2.6H_2O$ | 0.01 mg/L |
| $FeSO_4$ | 1.5 mg/L |
| $NaMoO_4$ | 2.0 mg/L |
| Fe EDTA | 5.0 mg/L |
| $KH_2PO_4$ | 20.0 mM |
| NaOH | to pH 7 |

The composition of the standard trace element solution is not critical but is standardized for all procedures to eliminate it as a variable.

Media A and the microorganism-containing soil is inoculated with 3.0 g/L D-threonine and incubated at 30° C. with shaking (200 rpm) for five days. A 1 mL sample is then subcultured into an identical shake-flask and again incubated as above until turbid. A 5 mL sample of the turbid culture then is inoculated into a chemostat with media A and 3.0 g/L D-threonine and maintained continuously for two weeks at a dilution rate of 0.03/minute. Liquid media from chemostat is subcultured onto an agar plate with media A and 15 g/L Noble Agar. After incubation for five days at 30° C., a single colony is isolated. The isolated strain is Gram-negative, rod-shaped, and identified by cell wall fatty acid composition as *Alcaligenes dentrificans xylosoxydans*. A sample of this microbe was deposited on Apr. 28, 1994, with the American Type Culture Collection (ATCC), 12301 Parklawn Drive, Rockville, Md. 20852 under ATCC No. 55564.

Fifty milliliters of media A containing 6.0 g/L D-threonine is inoculated with *Alcaligenes dentrificans xylosoxydans*. After the mixture is incubated at 37° C. for 48 hours, 10 mL of the mixture are subcultured into 250 mL of media A with 6.0 g/L D-threonine. After 40 hours of incubation at 37° C., the cells are concentrated to a paste by centrifugation at 10,000 G and washed with 50 mL phosphate buffer pH 7 and again concentrated to a paste by centrifugation at 10,000 G. The washed paste then is passed through a French Press at 17000 psi to rupture the cells and produce cell extract.

Cell debris is removed by centrifugation for one hour at 100,000 G and the enzyme-containing supernatant collected.

EXAMPLE 7

After enrichment of the racemic D,L-threo 2-amino-3-hydroxy-3-(4-methylthiophenyl)propionic acid mixtures or D,L-threo 2-amino-3-hydroxy-3-(4-methylsulfonylphenyl)propionic acid mixtures to the L-threo form, regeneration of the corresponding 4-methylthiobenzaldehyde or 4-methylsulfonylbenzaldehyde, respectively, from the aqueous solution is effected by lowering the pH to 0.5 with hydrochloric acid in order to cleave the Schiff base. The aldehyde thus formed is collected by filtration and recycled back into the condensation step.

EXAMPLE 8

A mixture of D- and L-threo 2-amino-3-hydroxy-3-(4-methylsulfonylphenyl)propionic acid (0.8 g) is combined with 10 mL of 50 mM sodium phosphate (pH 8.0), 0.5 mM pyridoxal-5-phosphate, and 20 mL of methylene chloride. Ten milliliters of crude D-threonine aldolase are added to initiate the reaction. After 90 minutes, the ee was 94%.

EXAMPLE 9

A mixture of D- and L-threo 2-amino-3-hydroxy-3-(4-methylsulfonylphenyl)propionic acid (2.0 g) is added to a 10 mL solution of 50 mM sodium phosphate (pH 8.0), 0.8 mM pyridoxal-5-phosphate, and 100 mM sodium chloride. Twenty grams of wet Amberlite XAD-16 resin are added, together with 10 mL of crude D-threonine aldolase. The reaction mixture is stirred for 120 minutes at 42° C. with vigorous mixing to produce L-threo 2-amino-3-hydroxy-3-(4-methylsulfonylphenyl)propionic acid with an ee of 96%.

What is claimed is:

1. A process for the enantiomeric enrichment of a mixture of D- and L-threo 2-amino-3-hydroxy-3-phenylpropionic acids of the formula:

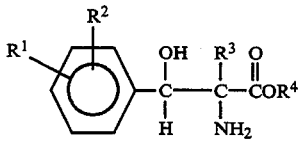

in which each of $R^1$ and $R^2$, independently of the other, is hydrogen, hydroxy, halo, nitro, trifluoromethyl, lower alkyl, lower alkoxy, lower alkylsulfonyl, lower alkylsulfinyl, or lower alkylthio;
$R^3$ is hydrogen or methyl; and
$R^4$ is hydrogen or a carboxylic acid protecting group; and
the salts thereof with base when $R^4$ is hydrogen, which comprises bringing said mixture into contact in an aqueous medium with D-threonine aldolase which is enzymatically active with respect to the D-threo enantiomer but substantially inactive with respect to the L-threo enantiomer, until the D-threo enantiomer is converted to the corresponding benzaldehyde and an amino acid derivative of the formula $R^3CH(NH_2)COOR^4$, while the L-threo enantiomer remains substantially unconverted.

2. The process according to claim 1 in which said D- and L-threo 2-amino-3-hydroxy-3-phenylpropionic acids are of the formula:

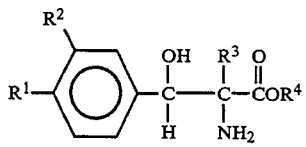

in which
each of $R^1$ and $R^2$, independently of the other, is hydrogen, hydroxy, methoxy, methylsulfonyl, or methylthio;
$R^3$ is hydrogen or methyl; and
$R^4$ is hydrogen, $C_1$–$C_3$ alkyl, or a cation.

3. The process according to claim 2 in which $R^1$ is methylthio and $R^2$ is hydrogen.

4. The process according to claim 2 in which $R^1$ is methylsulfonyl and $R^2$ is hydrogen.

5. The process according to claim 2 in which $R^3$ is methyl.

6. The process according to claim 2 wherein the L-threo enantiomer is recovered from the reaction mixture.

7. The process according to claim 2 wherein at least one of said benzaldehyde and said amino acid derivative is recovered from said reaction mixture.

8. The process according to claim 2 wherein said mixture is brought into contact with said D-threonine aldolase in the presence of at least one substance capable of removing either or both of said benzaldehyde and said amino acid derivative from the reaction mixture.

9. The process according to claim 8 wherein said removing substance is an organic solvent in which one of the reaction products is preferentially soluble.

10. The process according to claim 9 wherein said organic solvent includes at least one halogenated alkane, lower alkanone, or aromatic hydrocarbon.

11. The process according to claim 8 wherein said removing substance is a nonionic absorbent-type resin.

12. A process according to claim 1 further comprising (i) esterifying the stereoisomeric enriched L-threo 2-amino-3-hydroxy-3-(4-methylsulfonylphenyl)propionic acid to form an ester of 2-amino-3-hydroxy-3-(4-methylsulfonyl)phenylpropionic acid, (ii) reducing the ester to form 2-amino-3-hydroxy-3-(4-methylsulfonyl)phenyl-propane-1,3-diol, and (iii) dichloroacetylating said diol to form thiamphenicol.

13. A process according to claim 1 further comprising (i) esterifying L-threo 2-amino-3-hydroxy-3-(4-methylsulfonylphenyl)propionic acid to form an ester of 2-amino-3-hydroxy-3-(4-methylsulfonylphenyl)propionic acid, (ii) reducing said ester to form 3-(4-methylsulfonylphenyl)-2-aminopropane-1,3-diol, (iii) dichloroacetylating the diol to form D-threo 3-(4-methylsulfonylphenyl)-2-(dichloroacetamido)propane-1,3-diol, and (iv) fluorinating D-threo 3-(4-methylsulfonylphenyl)-2-(dichloroacetamido)propane-1,3-diol to form florfenicol.

14. A process according to claim 1 further comprising (i) esterifying the L-threo 2-amino-3-hydroxy-3-(4methylsulfonylphenyl)propionic acid to form an ester of 2-amino-3-hydroxy-3-(4-methylsulfonylphenyl)propionic acid, (ii) reducing the ester to form 2-amino-3-(4-methylsulfonylphenyl)propane-1,3-diol, (iii) protecting the 2-amino group of the diol with an amino-protecting group, (iv) fluorinating the 3-hydroxy group of the protected diol, (v) removing the amino-protecting group, and (vi) dichloroacetylating the unprotected amino group to form florfenicol.

15. In a process for the preparation of an L-threo 2-amino-3-hydroxy-3-phenylpropionic acid which is unsubstituted or substituted in the phenyl ring in which a correspondingly unsubstituted or substituted benzaldehyde is condensed with glycine and the D,L-threo enantiomeric forms of the resultant 2-amino-3-hydroxy-3-phenylpropionic acid thereafter are separated, the improvement comprising subjecting said enantiomeric forms of D,L-threo 2-amino-3-hydroxy-3-phenylpropionic acid to the action of D-threonine aldolase to preferentially cleave the D-threo 2-amino-3-hydroxy-3-phenylpropionic acid to glycine and the corresponding benzaldehyde.

16. The process according to claim 15 wherein the improvement further comprises removing the benzaldehyde and glycine and recycling at least one into the condensation step.

17. In the preparation of 2-amino-2-methyl-3-(3,4-dihydroxyphenyl)propionic acid in which an isomeric mixture of 2-amino-2-methyl-3-hydroxy-3-(3,4-dihydroxyphenyl)propionic acid having the D- and L-configuration about the α-carbon atom are resolved and the intermediate having the L-configuration about the α-carbon atom is hydrogenated to remove the hydroxy group in the 3-position, the improvement comprising subjecting said isomeric mixture to the action of a D-threonine aldolase to selectively cleave the isomer having the D-configuration about the α-carbon atom.

* * * * *